US010627327B2

(12) United States Patent
Makino et al.

(10) Patent No.: US 10,627,327 B2
(45) Date of Patent: Apr. 21, 2020

(54) MEMBRANE VESICLE RECOVERY DEVICE, MEMBRANE VESICLE RECOVERY METHOD, AND MEMBRANE VESICLE ANALYSIS METHOD

(71) Applicant: TOPPAN PRINTING CO., LTD., Tokyo (JP)

(72) Inventors: Yoichi Makino, Tokyo (JP); Shinji Irie, Ichihara (JP)

(73) Assignee: TOPPAN PRINTING CO., LTD., Tokyo (JP)

( * ) Notice: Subject to any disclaimer, the term of this patent is extended or adjusted under 35 U.S.C. 154(b) by 751 days.

(21) Appl. No.: 15/135,919

(22) Filed: Apr. 22, 2016

(65) Prior Publication Data
US 2016/0238497 A1    Aug. 18, 2016

Related U.S. Application Data

(63) Continuation of application No. PCT/JP2014/078405, filed on Oct. 24, 2014.

(30) Foreign Application Priority Data

Oct. 25, 2013 (JP) .................................. 2013-222751

(51) Int. Cl.
G01N 1/00       (2006.01)
G01N 1/40       (2006.01)
C12M 1/00       (2006.01)
B01L 3/00       (2006.01)
(Continued)

(52) U.S. Cl.
CPC .......... *G01N 1/4055* (2013.01); *B01L 3/5085* (2013.01); *C12M 47/06* (2013.01); *C12Q 1/68* (2013.01); *G01N 1/4005* (2013.01); *G01N 33/6842* (2013.01); *B01L 2300/069* (2013.01); *B01L 2300/0829* (2013.01);
(Continued)

(58) Field of Classification Search
CPC ............... G01N 1/4055; G01N 1/4005; G01N 33/6842; B01L 3/5085; C12M 47/06; C12Q 1/68
USPC ......................................................... 422/552
See application file for complete search history.

(56) References Cited

U.S. PATENT DOCUMENTS 6,899,863 B1    5/2005 Dhellin et al.
7,244,349 B2 *  7/2007 Vogel .................... B01L 3/5085
                                                    204/403.01
(Continued)

FOREIGN PATENT DOCUMENTS

CN    102037351 A    4/2011
JP    2002-535665    10/2002
JP    2003-531864    10/2003
(Continued)

OTHER PUBLICATIONS

International Search Report dated Jan. 27, 2015, in corresponding International Application No. PCT/JP2014/078405.
(Continued)

*Primary Examiner* — Jyoti Nagpaul

(57) ABSTRACT

A membrane vesicle recovery device includes: a liquid filler; and at least a fused membrane having a lipid bilayer membrane which covers at least a part of the outer periphery of the liquid filler, in which a content of a membrane vesicle is mixed into the liquid filler through fusing of the membrane vesicle and the fused membrane.

14 Claims, 15 Drawing Sheets

(51) Int. Cl.
*C12Q 1/68* (2018.01)
*G01N 33/68* (2006.01)

(52) U.S. Cl.
CPC ... *B01L 2300/0848* (2013.01); *B01L 2300/12* (2013.01); *B01L 2300/161* (2013.01); *B01L 2300/165* (2013.01)

(56) References Cited

U.S. PATENT DOCUMENTS

2005/0230272 A1* 10/2005 Lee .................. B01L 3/5027
205/792
2010/0304980 A1 12/2010 Takeuchi et al.

FOREIGN PATENT DOCUMENTS

| JP | 2005-185972 | 7/2005 |
|---|---|---|
| JP | 2010-517048 | 5/2010 |
| JP | 2010-534480 | 11/2010 |
| JP | 2011-516867 | 5/2011 |
| JP | 2011-524164 | 9/2011 |
| JP | 2013-7698 | 1/2013 |
| JP | 2013-102768 | 5/2013 |
| JP | 2013-516619 | 5/2013 |
| WO | WO 01/82958 A2 | 11/2001 |
| WO | WO 2008/092164 A2 | 7/2008 |
| WO | WO 2009/015357 A1 | 1/2009 |
| WO | WO 2009/146143 A2 | 12/2009 |
| WO | WO 2009/147519 A1 | 12/2009 |
| WO | WO 2011/083145 A1 | 7/2011 |

OTHER PUBLICATIONS

Chinese Office Action dated Dec. 23, 2016 in corresponding Chinese Patent Application No. 201480058099.9.

* cited by examiner

MEMBRANE VESICLE RECOVERY DEVICE, MEMBRANE VESICLE RECOVERY METHOD, AND MEMBRANE VESICLE ANALYSIS METHOD

CROSS REFERENCE TO RELATED APPLICATIONS

This application is a continuation application based on a PCT Patent Application No. PCT/JP2014/078405, filed Oct. 24, 2014, whose priority is claimed on Japanese Patent Application No. 2013-222751, filed Oct. 25, 2013, the entire content of which are hereby incorporated by reference.

BACKGROUND OF THE INVENTION

Field of the Invention

The present invention relates to an instrument and a method which relate to separation and analysis of membrane vesicles in the biological field, the biochemical field, the biotechnological field, the medical field, and the medicinal field.

Description of the Related Art

In the related art, in a structure such as a membrane vesicle from a living body such as a cell or a cell organelle or an artificial membrane vesicle covered by a lipid bilayer membrane, the content of this structure or a substance held on the lipid bilayer membrane has been analyzed.

In recent years, as a method for transmitting information between cells, a method using an exosome which is a vesicle having a lipid bilayer membrane has attracted attention.

Exosomes contain protein, mRNA, micro RNA (miRNA), DNA, or the like therein, and are membrane vesicles known to be able to transmit information to a destination cell by moving between cells. For example, it is known that in cells in which exosomes containing micro RNA from cancer cells are present, an immune function is activated or metastasis ability is acquired.

In exosomes, in addition to genetic information and other signal factors within cells from which exosomes are released, factors that control functions of other cells to which the exosomes are accepted are included. Therefore, it is considered that it is possible to utilize exosomes as a new biomarker source for diagnosing diseases.

For example, Japanese Unexamined Patent Application, First Publication No. 2013-102768 and Published Japanese Translation No. 2010-534480 of the PCT International Publication disclose that cancer or an adverse pregnancy outcome can be diagnosed by analyzing miRNA within an exosome.

Published Japanese Translation No. 2011-524164 of the PCT International Publication discloses that each RNA is measured for determining the efficiency of treatment using a small interfering RNA (siRNA) therapeutic agent or a miRNA therapeutic agent.

Published Japanese Translation No. 2013-516619 of the PCT International Publication discloses that a protein marker which becomes an indicator of risk of onset of a cardiovascular event is detected.

Published Japanese Translation No. 2010-517048 of the PCT International Publication discloses that a disease such as cancer or infertility associated with the production of an autoantibody can be diagnosed by measuring the level of immunoreactive autoantibody.

Japanese Unexamined Patent Application, First Publication No. 2013-7698 discloses that a vesicle stress response and a renal disease which is associated with the response can be detected by measuring aquaporin 1 of an exosome in urine.

An exosome can be prepared after being separated from a sample which can contain an exosome through separation such as ultracentrifugation or density gradient ultracentrifugation using a density difference. In addition, an exosome can also be separated through methods disclosed in Published Japanese Translation No. 2003-531864 of the PCT International Publication or Published Japanese Translation No. 2002-535665 of the PCT International Publication. In addition, a kit for separating and purifying an exosome is commercially available (for example, ExoQuick of System Biosciences, Inc. or Exosome Isolation of Life Technologies).

For example, in the case of separating an exosome through centrifugation, it is impossible to avoid impurities other than the exosome from being mixed in the separated exosome, and therefore, there is a limit to improve analysis accuracy and reproducibility.

In addition, in the ultracentrifugation, the density gradient ultracentrifugation, or the like, the work procedure for separating an exosome is complicated and it requires a long period of time to separate and purify an exosome.

In addition, a separation kit in the related art which simply separates an exosome has inferior reliability since purification of an exosome is insufficiently performed.

It is also known that an exosome is selectively separated and purified using tetraspanin existing in a lipid bilayer membrane of an exosome. Tetraspanin is, for example, a 4-pass transmembrane type membrane protein family known to have 33 members in a human. Particularly, CD9, CD63, and CD81 are known as exosome markers. However, in the case where an exosome is separated and purified using an anti-tetraspanin monoclonal antibody, in some cases, an ununiformity is caused in an exosome finally separated and purified depending on the type of antigen to be separated.

In addition, in some cases, the membrane structure of an exosome is destroyed in order to analyze the exosome. In this case, the content of the exosome is diluted in the exosome destruction process. Even if it is necessary to concentrate a product obtained by destroying an exosome in a diluted state, it is difficult to concentrate the product since there may be components which are degenerated or lost in the concentration process. In addition, in the case where protein of an exosome is to be analyzed, it is impossible to amplify protein to be analyzed in vitro unlike in the case of a nucleic acid. Therefore, it is necessary to analyze an exosome without diluting the exosome, if possible.

The present invention has been made in consideration of the above-described circumstances, and an object of the present invention is to provide a membrane vesicle recovery device in which a membrane vesicle is not destroyed and constituents of the membrane vesicle are barely diluted, and which can selectively recover a membrane vesicle; a membrane vesicle recovery method; and a membrane vesicle analysis method which is simple and is excellent in accuracy and reproducibility.

SUMMARY

A membrane vesicle recovery device according to a first embodiment of the present invention includes: a liquid filler; and at least a fused membrane including a lipid bilayer membrane which covers at least a part of an outer periphery of the liquid filler, in which a content of a membrane vesicle is mixed into the liquid filler through fusing of the membrane vesicle and the fused membrane.

The membrane vesicle recovery device according to the above-described first embodiment may further include: a reaction base having a surface on which a plurality of holding sections which is configured to hold the liquid filler are formed, in which the liquid filler is covered with the fused membrane in each of the holding sections.

In the above-described first embodiment, the holding sections may be recessed sections formed in the reaction base, in the recessed sections, the fused membrane may come into contact with an opening end forming a boundary between the surface and each of the recessed sections and may be provided in the reaction base so as to block the recessed sections, and the recessed sections may be filled with the liquid filler.

In the above-described first embodiment, a plurality of the fused membranes may be provided in the reaction base so as to come into contact with a part along the opening end in the inner wall surface of the recessed sections and to individually block each of the plurality of recessed sections.

In the above-described first embodiment, in the reaction base, at least the inner wall surface may be hydrophobic and a hydrophobic section of the fused membrane may come into contact with the inner wall surface.

In the above-described first embodiment, the fused membrane may be formed in a planar shape along the surface and formed in a series of membrane shape which blocks recessed sections.

In the above-described first embodiment, the fused membrane may contain a membrane charge adjustment substance promoting membrane fusion between the fused membrane and the membrane vesicle which is derived from a living body or an artificial vesicle and which is covered by the lipid bilayer membrane.

In the above-described first embodiment, the membrane charge adjustment substance may contain at least one of a membrane-destroying peptide, a membrane fusogenic polymer, a pH-sensitive polymer, and virus-derived membrane fusion protein.

In the above-described first embodiment, the liquid filler may contain a solvent and a reaction reagent for biochemical analysis contained in the solvent.

In the above-described first embodiment, the reaction reagent for biochemical analysis may contain a pH indicator.

In the above-described first embodiment, the liquid filler may be a gel or sol.

The membrane vesicle recovery device according to the above-described first embodiment may further include: a reaction base which has a surface on which a plurality of hydrophilic sections and hydrophobic sections surrounding the hydrophilic sections are formed, in which the liquid filler is provided in the hydrophilic sections, and the fused membrane comes into contact with the hydrophobic sections in a boundary between each of the hydrophilic sections and each of the hydrophobic sections and wraps the liquid filler.

A membrane vesicle recovery method according to a second embodiment of the present invention is a membrane vesicle recovery method for recovering a membrane vesicle which is derived from a living body or an artificial vesicle and which is covered by a lipid bilayer membrane in the membrane vesicle recovery device according to the above-described first embodiment. The method includes: subjecting the fused membrane and the membrane vesicle to membrane fusion by bringing a sample containing the membrane vesicle into contact with the fusion membrane.

The membrane vesicle recovery method according to the second embodiment of the present invention may further include: adding a pH regulator which makes the sample acidic to the sample, and then, bringing the acidic sample into contact with the fused membrane.

A membrane vesicle analysis method according to a third embodiment of the present invention is a membrane vesicle recovery method for analyzing the content, membrane protein, or a membrane lipid of a membrane vesicle which is derived from a living body or an artificial vesicle and which is covered by a lipid bilayer membrane. The method includes: fusing the membrane vesicle into the fused membrane of the membrane vesicle recovery device according to the above-described first embodiment; and holding the membrane protein or the membrane lipid on the membrane vesicle at the fused membrane.

A membrane vesicle analysis method according to a fourth embodiment of the present invention is a membrane vesicle recovery method for analyzing the content, membrane protein, or a membrane lipid of a membrane vesicle which is derived from a living body or an artificial vesicle and which is covered by a lipid bilayer membrane. The method includes: fusing the membrane vesicle into the fused membrane of the membrane vesicle recovery device according to according to the above-described first embodiment; and reacting the reaction reagent for biochemical analysis with the content, membrane protein, or a membrane lipid of the membrane vesicle within the liquid filler.

In the membrane vesicle analysis method using the membrane vesicle recovery device according to the above-described first embodiment or the membrane vesicle analysis method according to the above-described fourth embodiment, the reaction reagent for biochemical analysis may contain at least one of a nucleic acid analysis reagent, an invader reaction reagent, a protein analysis reagent, a lipid analysis reagent, an immunoassay reagent, and a homogeneous antigen-antibody reaction reagent.

According to the above-described embodiments of the present invention, it is possible to provide a membrane vesicle recovery device and a membrane vesicle recovery method in which constituents of the membrane vesicle are barely diluted, and which can selectively recover a membrane vesicle, and a membrane vesicle analysis method that is simple, and is excellent in accuracy and reproducibility.

DETAILED DESCRIPTION OF THE PREFERRED EMBODIMENTS

First Embodiment

Figure 1:
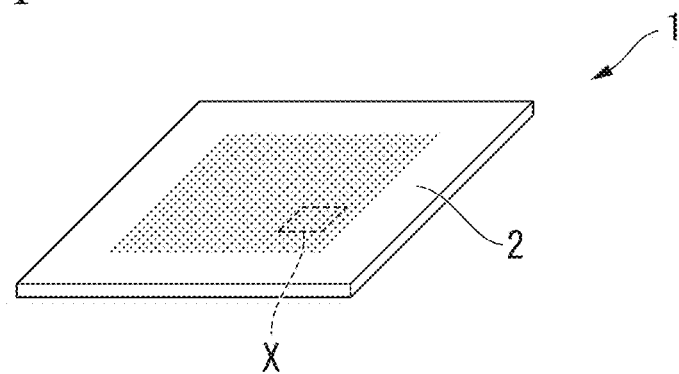
FIG. 1 is a perspective view showing a membrane vesicle recovery device according to a first embodiment of the present invention.
Figure 2:
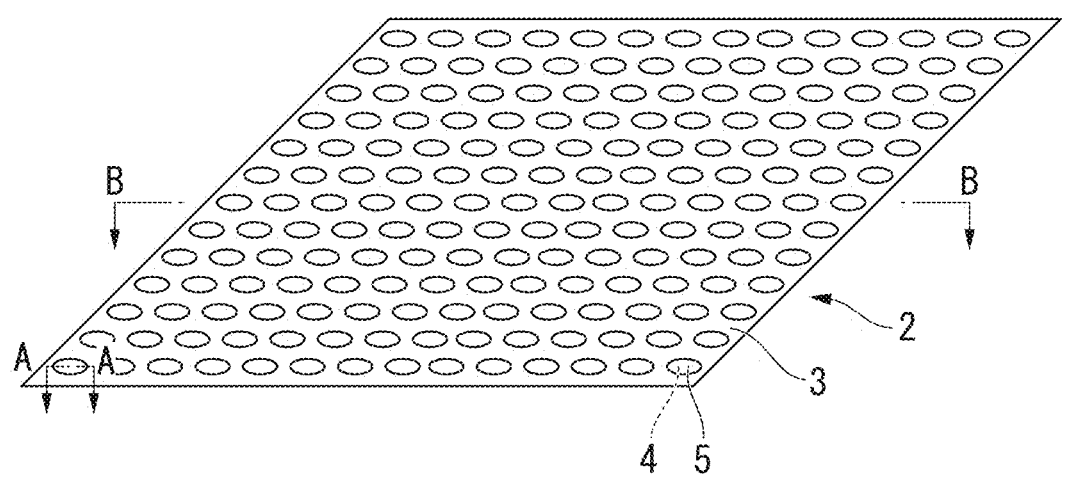
FIG. 2 is an enlarged view of the section shown by a reference numeral X in FIG. 1.
Figure 3A:
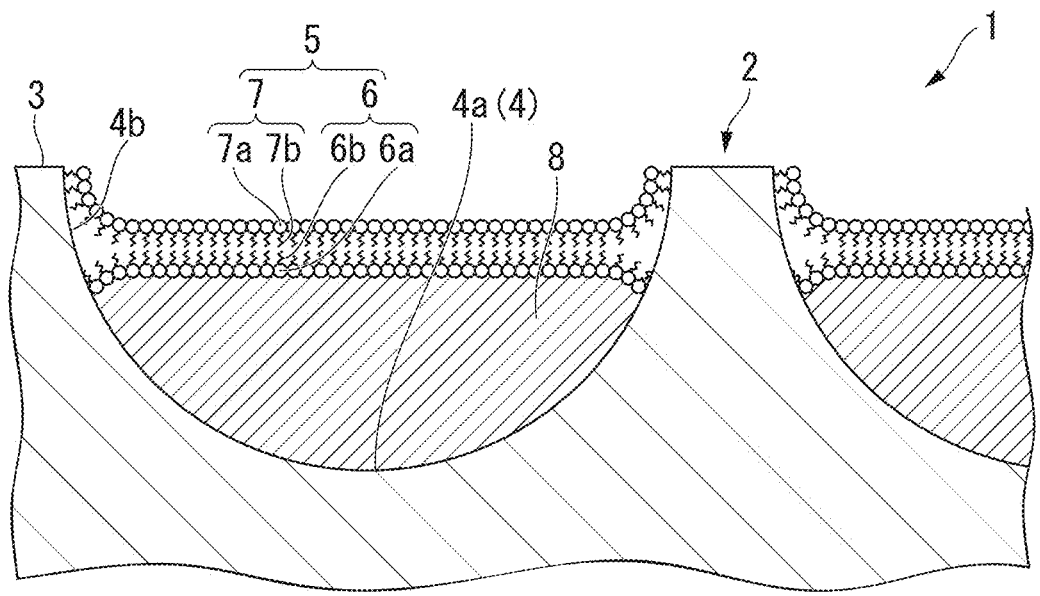
FIG. 3A is a schematic cross-sectional view taken along line A-A of FIG. 2.
Figure 3B:
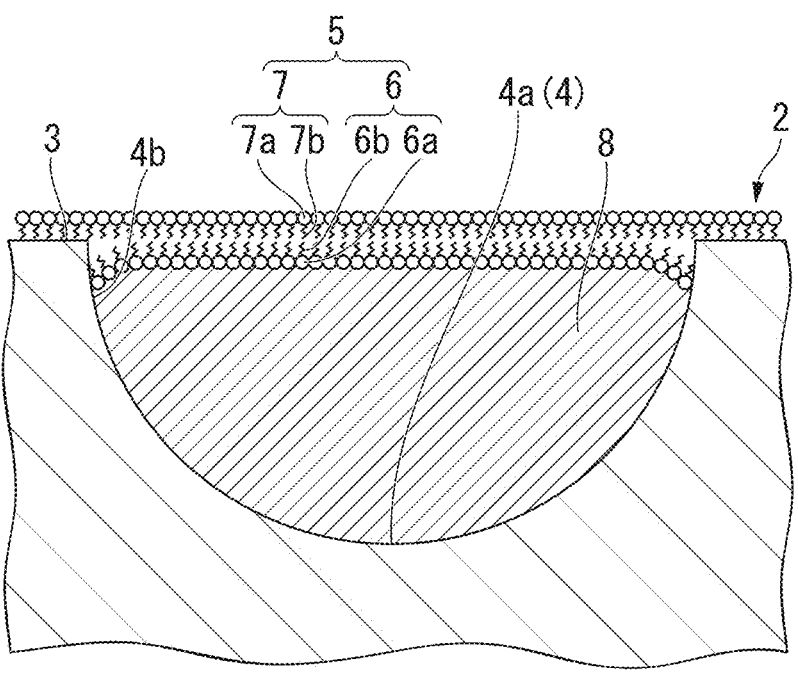
FIG. 3B is a cross-sectional view showing another configuration example of the membrane vesicle recovery device according to the first embodiment of the present invention.

A first embodiment of the present invention will be described. FIG. 1 is a perspective view showing a membrane vesicle recovery device of this embodiment. FIG. 2 is an enlarged view of the section shown by a reference numeral X in FIG. 1. FIG. 3A is a schematic cross-sectional view taken along line A-A of FIG. 2.

As shown in FIGS. 1 to 3B, a membrane vesicle recovery device 1 of this embodiment includes a reaction base 2, a fused membrane 5, and a filler 8.

The reaction base 2 is a plate member in which a plurality of recessed sections 4 are formed on a surface 3. In the reaction base 2, an opening end 4b of a recessed section 4 and the surface 3 are hydrophobic. In this embodiment, the reaction base 2 is made of glass or silicon. A fine well which forms a recessed section 4 is produced on the surface of the reaction base 2 after the surface of the reaction base 2 is subjected to hydrophobic processing through disilazane processing. In this embodiment, an inner wall surface 4a of the recessed section 4 is hydrophilic.

The fused membrane 5 is a lipid bilayer membrane which covers the recessed section 4. That is, the fused membrane 5 has a first layer 6 which is positioned at a position close to the reaction base 2 and a second layer 7 which is stacked on the first layer 6. The first layer 6 and the second layer 7 respectively have hydrophilic sections 6a and 7a and hydrophobic sections 6b and 7b. The fused membrane 5 comes into contact with the opening end 4b which forms a boundary between the recessed section 4 and the surface 3 of the reaction base 2 in the recessed section 4. The fused membrane 5 of this embodiment is coupled to a section along the opening end 4b of the recessed section 4 in the inner wall surface 4a of the recessed section 4. In addition, in this embodiment, a plurality of fused membranes 5 are respectively provided with respect to the recessed sections 4 of the reaction base 2 so as to individually block the plurality of recessed sections 4.

In a recessed section 4, the hydrophobic sections of a fused membrane 5, the opening end 4b of the recessed section 4, and the hydrophobic surface 3 are coupled to each other.

The filler 8 is a liquid with which the recessed section 4 is filled. In addition, the filler 8 may be a gel or sol. It is preferable that the filler 8 have a composition in which degeneration or decomposition does not occur with respect to a membrane vesicle to be recovered. In addition, the filler 8 may contain a substance for decomposing or inactivating a substance which affects analysis in the membrane vesicle to be recovered. In addition, in this embodiment, there is an aqueous solvent (not shown) on the surface opposite to the surface facing the filler 8 of the fused membrane 5.

Next, a method for producing the membrane vesicle recovery device 1 of this embodiment will be described. FIGS. 4 to 12 are views illustrating a process of producing the membrane vesicle recovery device 1.

Figure 4:
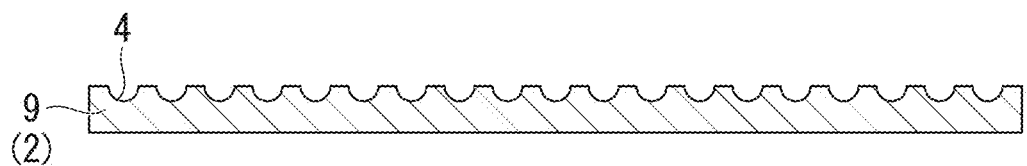
FIG. 4 is a view illustrating a production process of the membrane vesicle recovery device according to the first embodiment of the present invention.

First, the reaction base 2 is molded. The reaction base 2 is molded by disposing the recessed sections 4, which have a size large enough to house a membrane vesicle such as an exosome 11, in an array shape with respect to a base material 9 formed of plate-like glass or a plate-like resin member, as shown in FIG. 4. The array of the recessed sections 4 is formed in the base material 9 through transference of the recessed sections to the base material 9 using a mold, or through cutting of the base material 9.

The recessed sections 4 may have a shape with, for example, a diameter of 1 μm and a depth of 1 μm.

In addition, in the case where the base material 9 is formed of a hydrophilic material, hydrophobic processing is performed on the outer surface of the base material 9 after the recessed sections 4 are molded. The hydrophobic processing is reforming of the surface, for example, disilazane processing performed on the outer surface of the base material 9.

Figure 5:
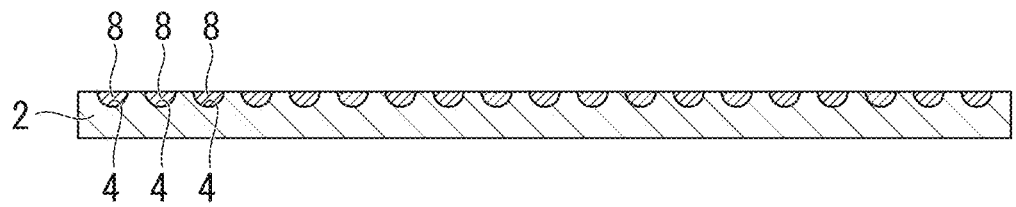
FIG. 5 is a view illustrating a production process of the membrane vesicle recovery device according to the first embodiment of the present invention.
Figure 6:
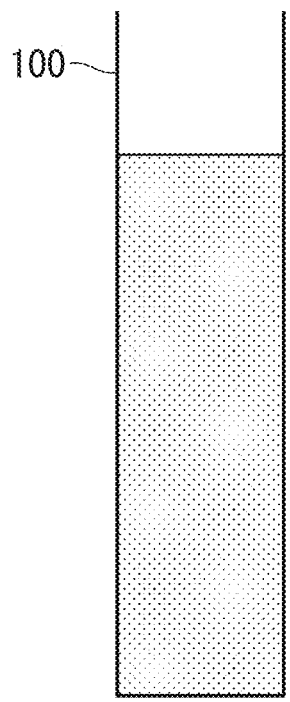
FIG. 6 is a view illustrating a production process of the membrane vesicle recovery device according to the first embodiment of the present invention.

Next, as shown in FIGS. 4 and 5, a recessed section 4 formed in the reaction base 2 is filled with the filler 8. The filler 8 may be a liquid within a water tank 100 in a process in which the fused membrane 5 is coupled to the recessed section 4 and which will be described below.

Next, the fused membrane 5 which blocks a recessed section 4 is coupled to each of the recessed sections 4. The fused membrane 5 is formed of a two-dimensional solid membrane 10 (refer to FIG. 7) which is obtained by dissolving amphipathic molecules such as arachidonic acids or stearic acids in an organic solvent which is then developed on the water surface in the water tank 100 shown in FIG. 6, and by compressing the molecules using a barrier. This two-dimensional solid membrane 10 is a monomolecular membrane constituting the first layer 6 and the second layer 7 in the lipid bilayer membrane. In a state in which the two-dimensional solid membrane 10 is formed on the water surface, a hydrophilic section 10a comes into contact with the water surface and a hydrophobic section 10b is exposed to outside air.

Figure 7:
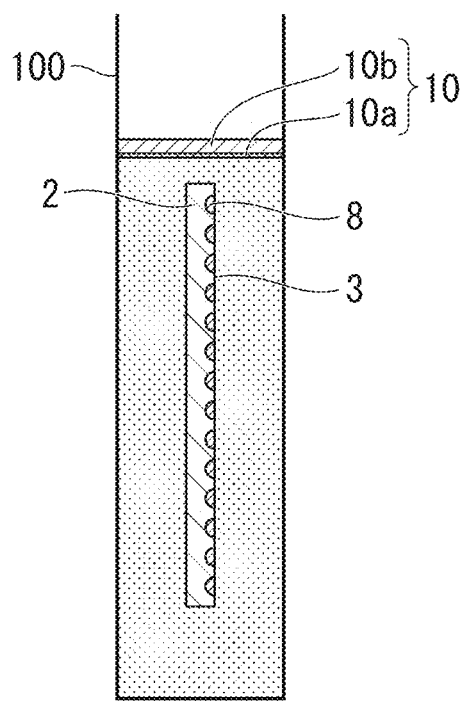
FIG. 7 is a view illustrating a production process of the membrane vesicle recovery device according to the first embodiment of the present invention.
Figure 8:
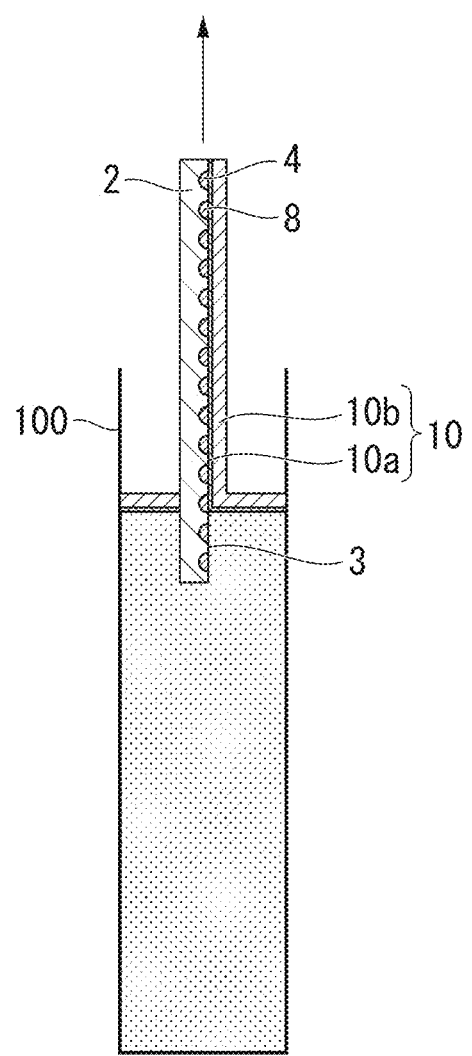
FIG. 8 is a view illustrating a production process of the membrane vesicle recovery device according to the first embodiment of the present invention.
Figure 9:
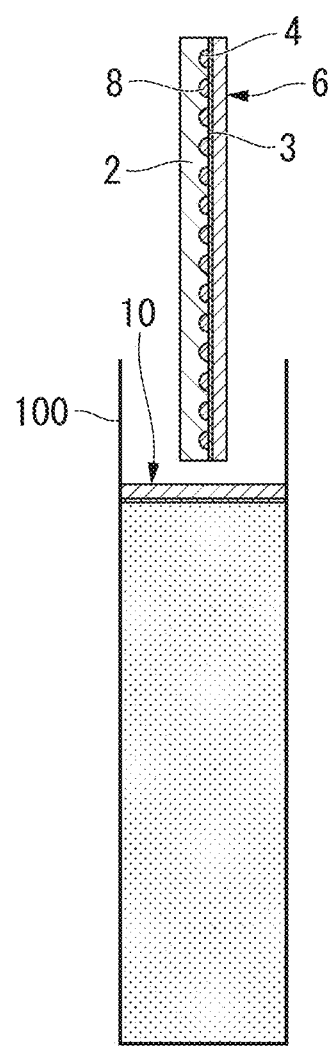
FIG. 9 is a view illustrating a production process of the membrane vesicle recovery device according to the first embodiment of the present invention.

In order to couple the fused membrane 5 to the reaction base 2, first, as shown in FIG. 7, the above-described two-dimensional solid membrane 10 is formed on the water surface after holding the reaction base 2 in the water tank 100. Subsequently, as shown in FIG. 8, the reaction base 2 in the water tank 100 is pulled up from the water tank 100 while maintaining the two-dimensional solid membrane 10 on the water surface to be in a solid state. The two-dimensional solid membrane 10 is adhered to the surface 3 of the reaction base 2 such that the two-dimensional solid membrane 10 covers the recessed sections 4 of the surface 3 of the reaction base 2 by pulling up the reaction base 2 such that the surface 3 on which the recessed sections 4 in the reaction base 2 are formed became vertical. As shown in FIG. 9, the two-dimensional solid membrane 10 which had been adhered to the reaction base 2 became a first layer 6 of the fused membrane 5.

Figure 10:
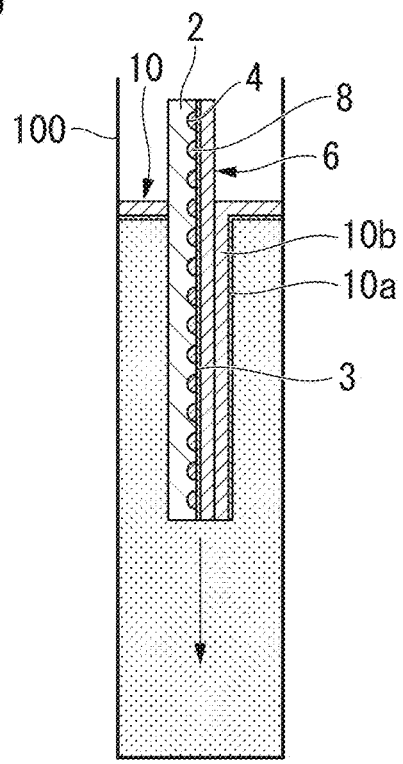
FIG. 10 is a view illustrating a production process of the membrane vesicle recovery device according to the first embodiment of the present invention.

After the two-dimensional solid membrane 10 covers the recessed sections 4 and is adhered to the surface 3 of the reaction base 2, as shown in FIG. 10, the reaction base 2 is inserted into the water tank 100 again. At this time, the above-described two-dimensional solid membrane 10 exists on the water surface.

Figure 11:
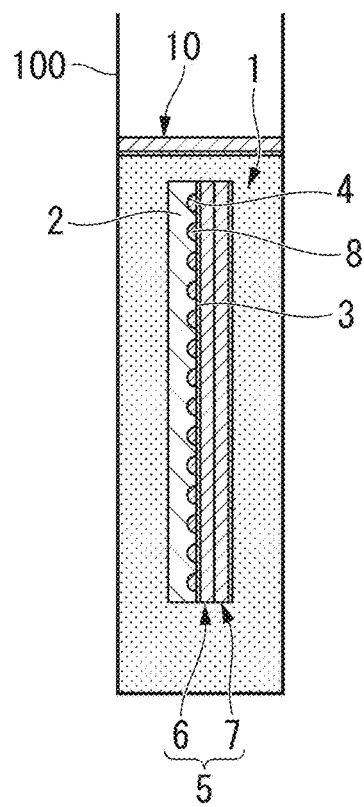
FIG. 11 is a view illustrating a production process of the membrane vesicle recovery device according to the first embodiment of the present invention.

As shown in FIG. 11, the hydrophobic section 10b of the two-dimensional solid membrane 10 formed on the water surface is brought into contact with the hydrophobic section 6b of the first layer 6 through the insertion of the reaction base 2 into the water tank 100, and the second layer 7 of the fused membrane 5 is formed so as to cover the recessed sections 4 on the surface 3 of the reaction base 2.

Figure 12:
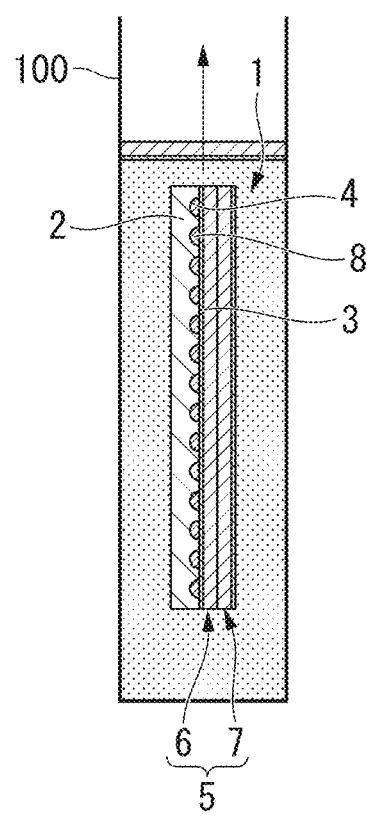
FIG. 12 is a view illustrating a production process of the membrane vesicle recovery device according to the first embodiment of the present invention.

After the first layer 6 and the second layer 7 of the fused membrane 5 are formed on the surface 3 of the reaction base 2, as shown in FIG. 12, the two-dimensional solid membrane 10 is removed from the water surface, and then, the membrane vesicle recovery device 1 is pulled up from the water tank 100. In sections which are not the recessed sections 4 on the surface 3 of the reaction base 2, the first layer 6 of the fused membrane 5 is removed from the surface 3 due to a weak coupling force of hydrophilic section 6a in the first layer 6 of the fused membrane 5 with respect to the surface 3 which is subjected to hydrophobic processing. Then, a section in the vicinity of the opening end 4b of a recessed section 4 is coupled to the hydrophobic section 6b of the fused membrane 5 (refer to FIG. 3A). Therefore, a plurality of recessed sections 4 are individually blocked by fused membranes 5. In addition, in some cases, the hydrophobic section 7b of a fused membrane 5 becomes a state of being coupled to the surface 3 (refer to FIG. 3B). Even in this case, a plurality of recessed sections 4 are blocked.

Figure 13:
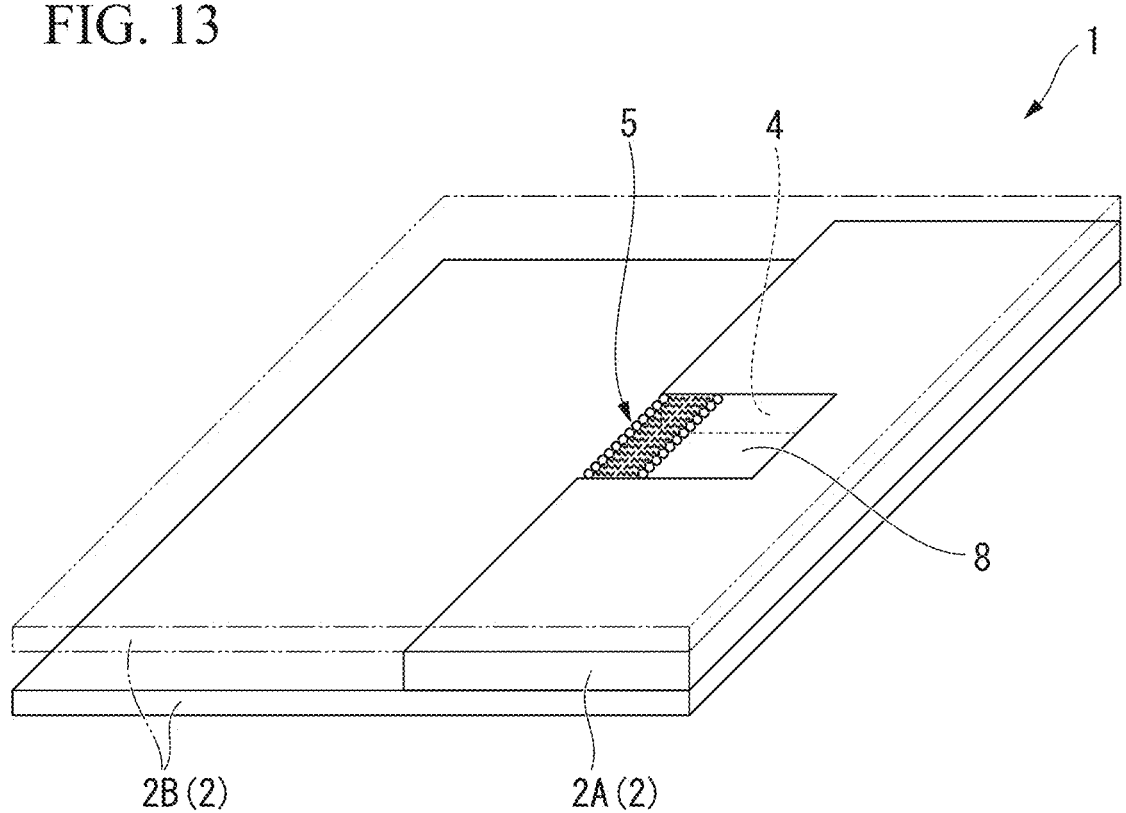
FIG. 13 is a schematic view showing another configuration example of the membrane vesicle recovery device according to the first embodiment of the present invention.

The recessed section 4 included in the reaction base 2 in this embodiment may not be formed in the vertical direction. For example, the recessed section 4 may be formed in, for example, the horizontal direction with respect to the surface direction of the reaction base 2, as shown in FIG. 13.

That is, the reaction base 2 may have an intermediate layer 2A in which a recessed section 4 is formed and a pair of outer layers 2B interposing the intermediate layer 2A therebetween, and the fused membrane 5 may be formed in the recessed section 4 which is formed in the intermediate layer 2A. As a method for forming a lipid bilayer membrane to be provided in the reaction base 2, a method disclosed in Japanese Unexamined Patent Application, First Publication No. 2009-128206 or the like can be used in addition to the above-described method.

Figure 14A:
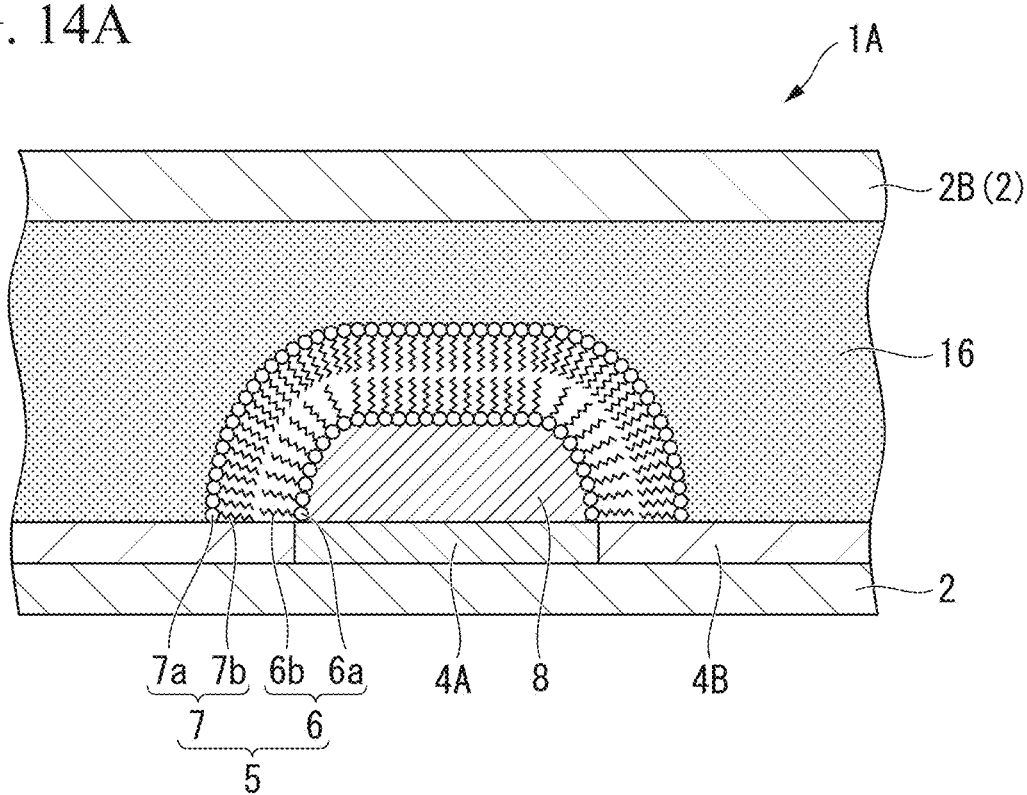
FIG. 14A is a schematic view showing still another configuration example of the membrane vesicle recovery device according to the first embodiment of the present invention.
Figure 14B:
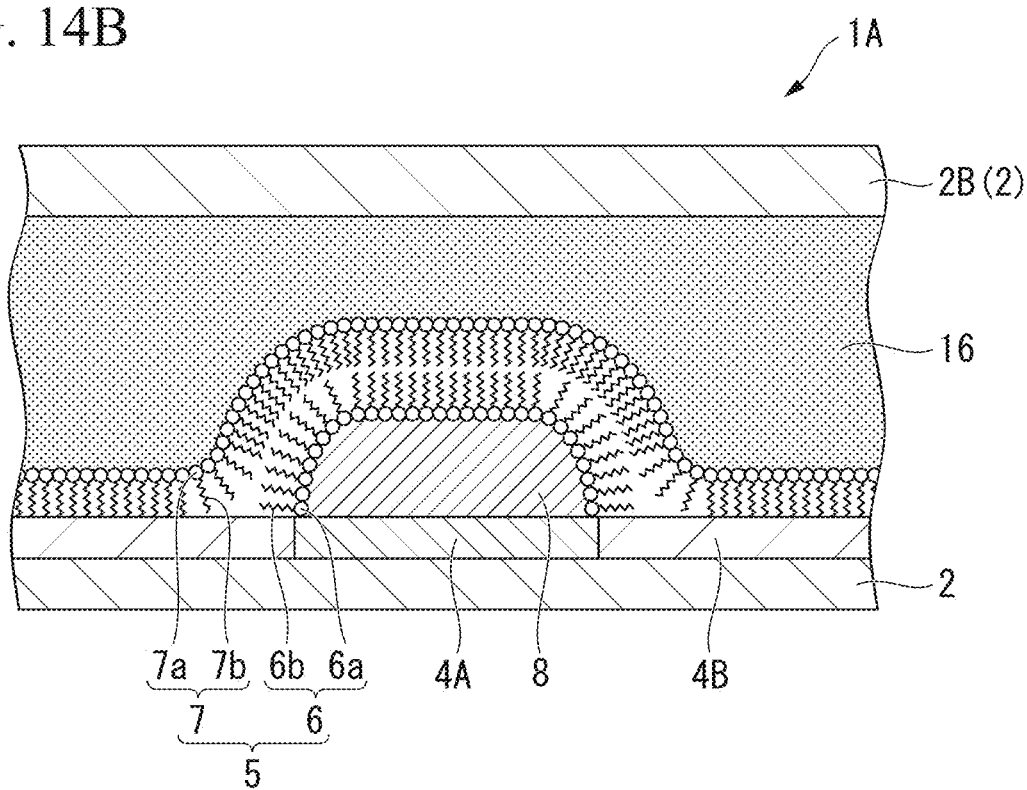
FIG. 14B is a schematic view showing still another configuration example of the membrane vesicle recovery device according to the first embodiment of the present invention.

In addition, the reaction base 2 in this embodiment need not have a recessed section 4. For example, the reaction base may have a hydrophilic section 4A and a hydrophobic section 4B on a plane, as shown in FIG. 14A or 14B, instead of the recessed section 4. In this case, the hydrophilic section 4A functions as the above-described recessed section 4. That is, the filler 8 remains in the hydrophilic section 4A having hydrophilic properties, the fused membrane 5 is provided so as to cover the filler 8, and the fused membrane 5 is coupled to the hydrophobic section 4B in the vicinity of a boundary between the hydrophilic section 4A and the hydrophobic section 4B.

A tool having such a configuration can be produced by, for example, forming a lipid bilayer membrane on the surfaces of liquid droplets provided on a plane through the method disclosed in Japanese Unexamined Patent Application, First Publication No. 2009-128206. Specifically, after pouring the filler 8 between the outer layers 2B shown in FIGS. 14A and 14B, an organic solvent containing a lipid solution is poured thereinto, and a buffer solution containing no lysate is then poured thereinto. As such, it is possible to form the fused membrane 5 of a lipid bilayer membrane that covers the outer surface of the filler 8. The fused membrane 5 has any shape shown in FIG. 14A or 14B depending on the hydrophobicity of the hydrophobic section 4B of the reaction base 2 and the type of solute.

Next, a membrane vesicle recovery method using the membrane vesicle recovery device 1 will be described.

Figure 15:
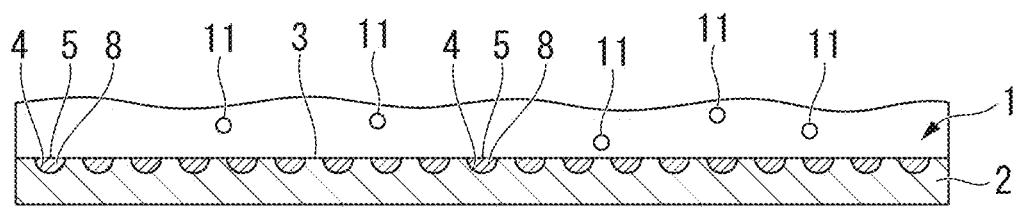
FIG. 15 is a view illustrating a membrane vesicle recovery method in which the membrane vesicle recovery device according to the first embodiment of the present invention is used.
Figure 16:
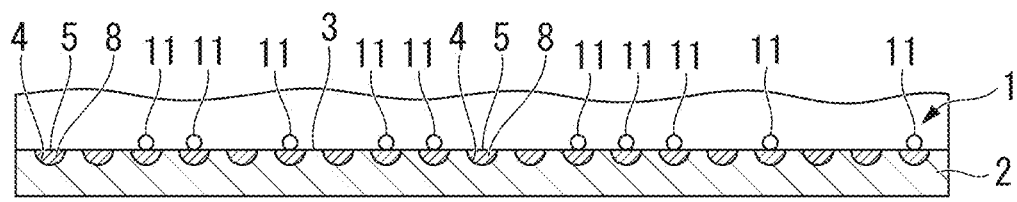
FIG. 16 is a view illustrating a membrane vesicle recovery method in which the membrane vesicle recovery device according to the first embodiment of the present invention is used.
Figure 17:
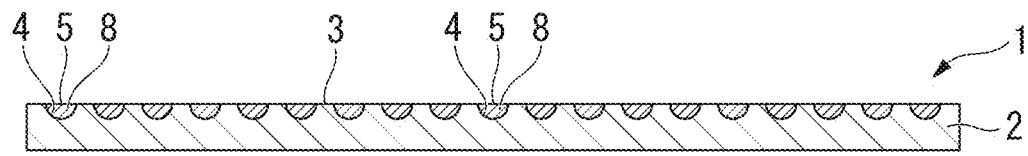
FIG. 17 is a view illustrating a membrane vesicle recovery method in which the membrane vesicle recovery device according to the first embodiment of the present invention is used.

FIGS. 15 to 17 are views illustrating the membrane vesicle recovery method using the membrane vesicle recovery device 1.

The membrane vesicle recovery method of the present embodiment is a method for recovering a membrane vesicle which is derived from a living body or an artificial vesicle and which is covered by the lipid bilayer membrane in the membrane vesicle recovery device 1 of this embodiment.

In this embodiment, an example of recovering an exosome 11 is shown as an example of recovering a membrane vesicle.

First, a sample which can contain an exosome 11 is prepared. The sample which can contain an exosome 11 may be, for example, a body fluid or a culture supernatant of a culture cell. In addition, a solution which is artificially prepared and contains liposome may be used as the sample.

Subsequently, the fused membrane 5 and the exosome 11 are subjected to membrane fusion by bringing the sample into contact with the fused membrane 5, as shown in FIGS. 15 and 16.

In the reaction base 2 in which recessed sections 4 are arranged in an array shape, the fused membrane 5 which is formed of a lipid bilayer membrane that blocks each of the recessed sections 4 is coupled to an inner wall surface 4a (refer to FIGS. 3A and 3B) of each of the recessed sections 4. Thus, if a membrane vesicle such as an exosome 11 approaches the fused membrane 5, the content of the membrane vesicle such as the exosome 11 is moved to the inside of each of the recessed sections 4 through membrane fusion (refer to FIG. 17). In the process in which the content of the membrane vesicle is moved to the inside of each of the recessed sections 4, the inside of the exosome 11 and the external environment are separated by the lipid bilayer membrane in a state in which the inside of the exosome 11 and the inside of each of the recessed sections 4 communicate with each other. Thus, each of the recessed sections 4 becomes a container in which the contents of exosomes 11 are accommodated, and are blocked and closed by the lipid bilayer membrane, after the fusion of the exosomes 11 without diffusion of the contents of exosomes 11 in the external environment.

Although the membrane fusion by the lipid bilayer membrane is a spontaneous nature of the lipid bilayer membrane, a repulsive force (repelling force) by a negative electric charge of a phosphate group of a phospholipid constituting the membrane blocks the membrane fusion. A negative electric charge on the membrane of the exosome 11 and a negative electric charge of the fused membrane 5 may be combined with each other in order to make the membrane vesicle such as the exosome 11 be fused into the fused membrane 5 at a high frequency. However, the negative electric charge on the exosome 11 depends on the membrane protein of the exosome 11, and therefore, the adjustment of the negative electric charge of the fused membrane 5 in combination with the exosome 11 can be complicated.

It is important to shorten the physical distance between the membrane vesicle and the fused membrane 5 in order to fuse the membrane vesicle into the fused membrane 5 at a high frequency. In the case where the volume of a solution containing exosomes 11 is small, the physical distance between an exosome 11 and the fused membrane 5 is shortened, and therefore, the frequency at which the exosome 11 comes into contact with the fused membrane 5 becomes high. In addition, even in the case where the concentration of exosomes 11 in the solution containing the exosomes 11 is high, the frequency at which an exosome 11 comes into contact with the fused membrane 5 becomes high. In addition, there is also a high possibility that a plurality of exosomes 11 are recovered in one recessed section 4 if only the concentration of exosomes 11 is increased.

It is possible to increase the efficiency of membrane fusion even by bringing a sample which has become acidic after adding a pH regulator that makes the sample acidic into contact with the fused membrane 5.

Next, a membrane vesicle analysis method using the membrane vesicle recovery device 1 of this embodiment will be described.

The membrane vesicle recovery device 1 of this embodiment can analyze molecules as constituents of an exosome 11 after trapping a membrane vesicle such as the exosome 11 in the recessed section 4.

In this embodiment, by fusing the membrane vesicle such as the exosome 11 into the fused membrane 5 of the membrane vesicle recovery device 1, the content of the exosome 11 is held in the filler 8 and membrane protein or a membrane lipid of the exosome 11 is held on the fused membrane 5.

Thus, it is possible to analyze the constituents of the exosome 11 in each of the recessed sections 4. Examples of analysis of transmembrane protein or the like which is held on the fused membrane 5 include immunoassay. Specific examples of the analysis method include determination of the quantity of CD9, CD63, and CD81, which are known to be highly expressed in the exosome 11. CD9, CD63, and CD81 are held on the fused membrane 5 through fusing of the exosome 11 into the fused membrane 5, and therefore, it is possible to perform quantitative determination using an anti-CD9 antibody, an anti-CD63 antibody, and an anti-CD81 antibody.

According to the membrane vesicle analysis method of this embodiment, it is possible to perform detection and quantitative determination of biomolecules derived from a membrane vesicle in the recessed sections 4. Accordingly, it is possible to perform a simple and accurate analysis with high reproducibility with respect to the constituents contained in the membrane vesicle.

Second Embodiment

Figure 18:
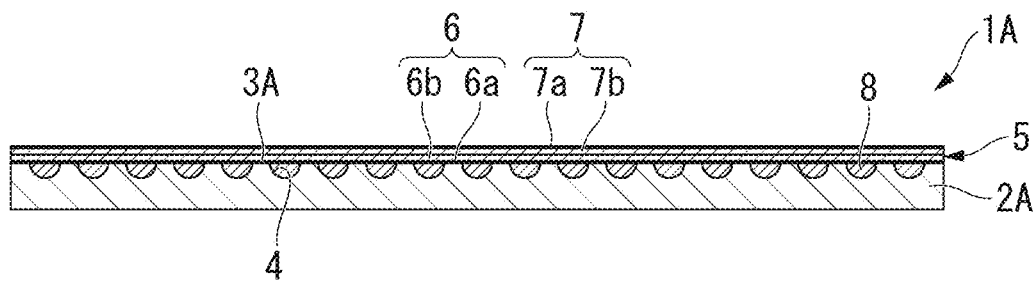
FIG. 18 is a schematic cross-sectional view showing a membrane vesicle recovery device according to a second embodiment of the present invention and is a cross-sectional view of the same line as line B-B of FIG. 2.
Figure 19:
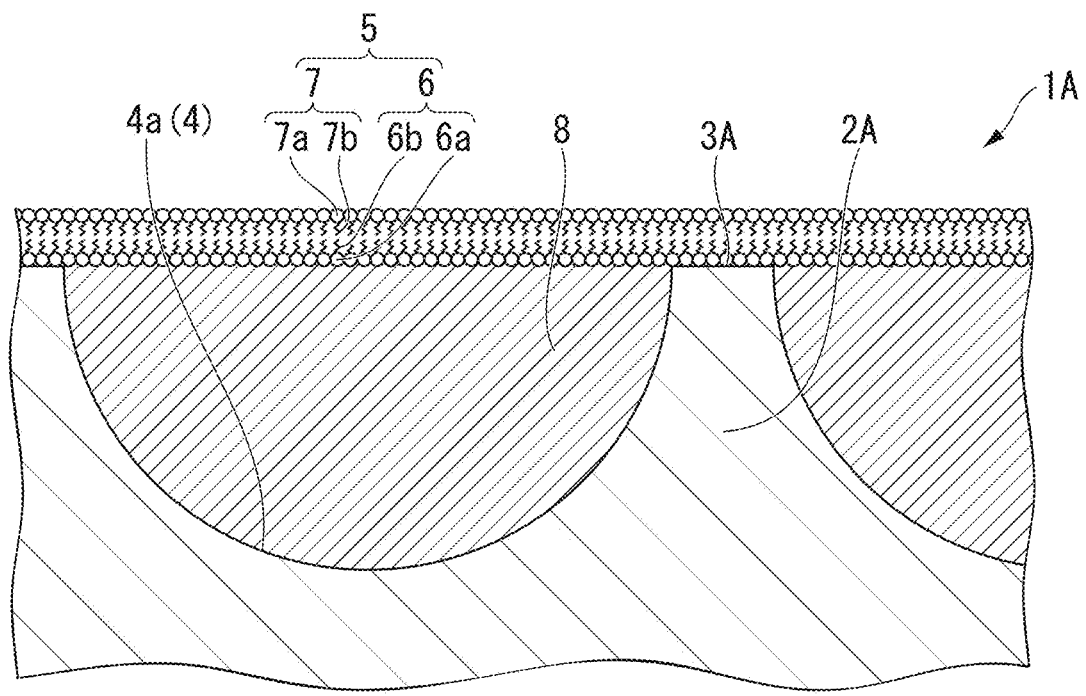
FIG. 19 is a schematic enlarged view of FIG. 18.

A second embodiment of the present invention will be described. FIG. 18 is a schematic cross-sectional view showing a membrane vesicle recovery device of this embodiment and is a cross-sectional view of the same line as line B-B of FIG. 2. FIG. 19 is a schematic enlarged view of FIG. 18.

As shown in FIGS. 18 and 19, a membrane vesicle recovery device 1A of this embodiment includes a reaction base 2A made of a different material from that of the reaction base 2, instead of the reaction base 2 described in the first embodiment.

In this embodiment, the surface 3A of the reaction base 2A is hydrophilic. For example, the reaction base 2A of this embodiment is formed of a hydrophilic material. In the case where the base material of the reaction base 2A is formed of a hydrophobic material, hydrophilic processing is performed on the outer surface of the base material after recessed sections 4 are molded. The hydrophilic processing is reforming of the surface, for example, plasma processing performed on the outer surface of the base material.

In this embodiment, the hydrophilic section of the fused membrane 5 is favorably coupled to the surface 3A of the reaction base 2A. Thus, the fused membrane 5 is formed in a planar shape along the surface 3A of the reaction base 2A and is formed in a series of membrane shapes which block the plurality of recessed sections 4.

Even with such a configuration, the same effect as that in the above-described first embodiment is exhibited.

Third Embodiment

Figure 20:
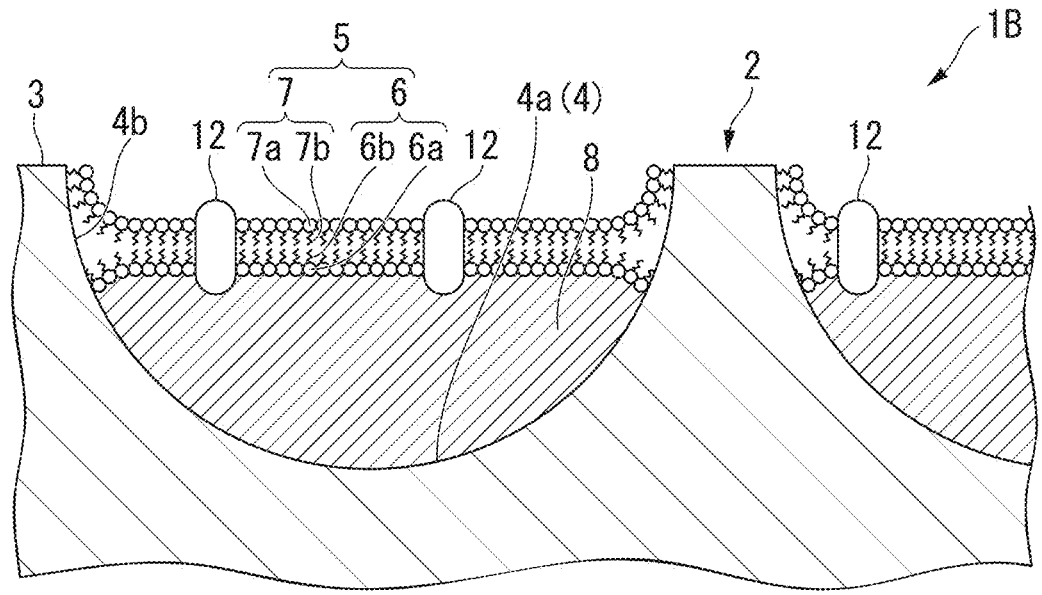
FIG. 20 is a schematic enlarged cross-sectional view showing a membrane vesicle recovery device according to a third embodiment of the present invention.

A third embodiment of the present invention will be described. FIG. 20 is a schematic enlarged cross-sectional view showing a membrane vesicle recovery device of this embodiment.

In a membrane vesicle recovery device 1B of this embodiment shown in FIG. 20, a fused membrane 5 contains a membrane charge adjustment substance 12 promoting fusion between a membrane vesicle and the fused membrane 5.

The membrane charge adjustment substance 12 contains at least one of a membrane-destroying peptide, a membrane fusogenic polymer, a pH-sensitive polymer, and virus-derived membrane fusion protein.

In the membrane vesicle recovery device 1B of this embodiment, when a solution containing exosomes is added to the fused membrane 5 so as to be brought into contact with the fused membrane 5, the membrane charge adjustment substance 12 incorporated into the fused membrane 5 promotes membrane fusion on the membrane vesicle by adjusting the membrane charge of the fused membrane 5.

In this embodiment, the recovery efficiency of a membrane vesicle such as an exosome is higher compared to the above-described first and second embodiments.

Fourth Embodiment

Figure 21:
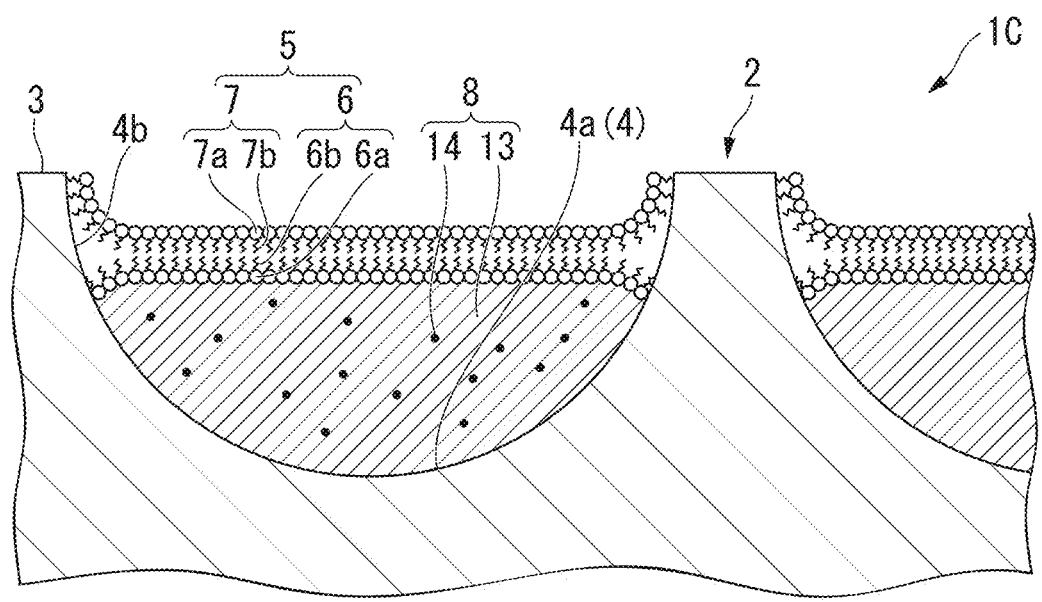
FIG. 21 is a schematic enlarged cross-sectional view showing a membrane vesicle recovery device according to a fourth embodiment of the present invention.

A fourth embodiment of the present invention will be described. FIG. 21 is a schematic enlarged cross-sectional view showing a membrane vesicle recovery device of this embodiment.

In a membrane vesicle recovery device 1C of this embodiment shown in FIG. 21, the filler 8 contains a solvent 13 and a reaction reagent for biochemical analysis 14 which is contained in the solvent 13. The reaction reagent for biochemical analysis 14 contains at least one of a nucleic acid analysis reagent, an invader reaction reagent, a protein analysis reagent, a lipid analysis reagent, an immunoassay reagent, and a homogeneous antigen-antibody reaction reagent.

In addition, in this embodiment, the filler 8 may be formed in a state in which the reaction reagent for biochemical analysis 14 is dissolved in an aqueous buffer as the solvent 13, or may be formed by being processed into a gel or sol. If the filler 8 is a gel or sol, it is difficult for the reaction reagent for biochemical analysis 14 to be diffused in the water tank 100 (refer to FIG. 7) when a reaction base 2 is put into the water tank 100 during the production of the membrane vesicle recovery device 1C.

Next, a membrane vesicle analysis method using the membrane vesicle recovery device 1C of this embodiment will be described.

The membrane vesicle analysis method of this embodiment is a method for analyzing the content, membrane protein, or a membrane lipid of a membrane vesicle from a living body or an artificial vesicle and which is covered by a lipid bilayer membrane within a recessed section 4.

In this embodiment, a membrane vesicle such as an exosome is fused into the fused membrane 5 in the same manner as that described in the above-described first embodiment.

In this embodiment, there is a reaction reagent for biochemical analysis 14 such as an enzyme or a substrate which reacts with an analysis object in the filler 8 with which a recessed section 4 has been filled in advance. Therefore, it is possible to cause a reaction in accordance with the type of reaction reagent for biochemical analysis 14 in the recessed section 4.

For example, in the case of detecting other nucleic acids such as micro RNA, an oligonucleotide, a polymerase, and a fluorescent reagent for detection may be put into the recessed section 4. Alternately, in the case of detecting protein, a homogeneous immunoassay reagent in which fluorescence resonance energy transfer (FRET) may occur through a sandwich reaction of antibodies labeled with fluorescence may be included in the recessed section 4.

In this embodiment, it is possible to analyze a substance within the recessed section 4 in a state in which external impurities do not enter the recessed section 4. Therefore, it is unnecessary to perform cleaning in order to remove impurities. Therefore, it is possible to eliminate the possibility that an analysis object is degenerated or lost through cleaning. Therefore, this embodiment is excellent in analysis accuracy and reproducibility compared to a method requiring cleaning in a process of separating and purifying an exosome 11 and a process of analyzing an exosome 11.

Furthermore, it is possible to rapidly perform a biochemical reaction on an analysis object incorporated into a recessed section 4 by making the recessed section 4 contain a reagent which is required for analysis. Therefore, it is possible to simply perform analysis on a substance or the like of which the activity is rapidly lost in an experiment system.

Furthermore, according to the membrane vesicle recovery device 1C, the membrane vesicle recovery method, and the membrane vesicle analysis method of this embodiment, the recessed section 4 contains the reaction reagent for biochemical analysis 14, and therefore, it is possible to simply and rapidly perform analysis on constituents of a membrane vesicle such as an exosome subsequently to separation of the membrane vesicle.

In addition, by performing detection of tetraspanin on the fused membrane 5 and biochemical analysis in recessed sections 4 together, it is possible to distinguish a recessed section 4 containing an exosome and a recessed section 4 containing no exosome among a plurality of recessed sections 4 on the reaction base 2 and to obtain biochemical analysis results obtained by targeting only the recessed section 4 containing an exosome.

It is possible to estimate how many exosomes are contained in one recessed section 4 by determining an amount of tetraspanin in each of the recessed sections 4.

Modification Example

Next, a modification example of the above-described embodiment will be described with reference to FIG. 21.

In this modification example, the reaction reagent for biochemical analysis 14 shown in FIG. 21 further contains a pH indicator in addition to the above-described reagent. In this modification example, it is possible to distinguish recessed sections 4 containing an exosome 11 and recessed sections 4 containing no exosome 11 among a plurality of recessed sections 4 on the reaction base 2 using the pH indicator.

In addition, by using the membrane vesicle recovery device 1 configured such that the volume of a recessed section 4 and the amount of pH indicator became constant with respect to each of the recessed sections 4, it is possible to estimate how many exosomes 11 are contained in one recessed section 4 using the pH indicator.

Fifth Embodiment

Figure 22:
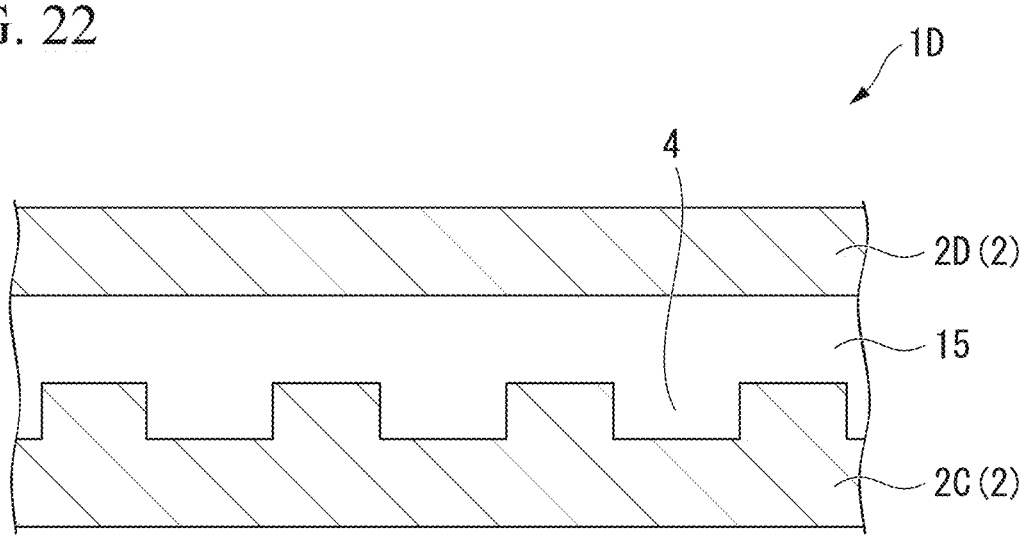
FIG. 22 is a schematic enlarged cross-sectional view showing a membrane vesicle recovery device according to a fifth embodiment of the present invention.
Figure 23:
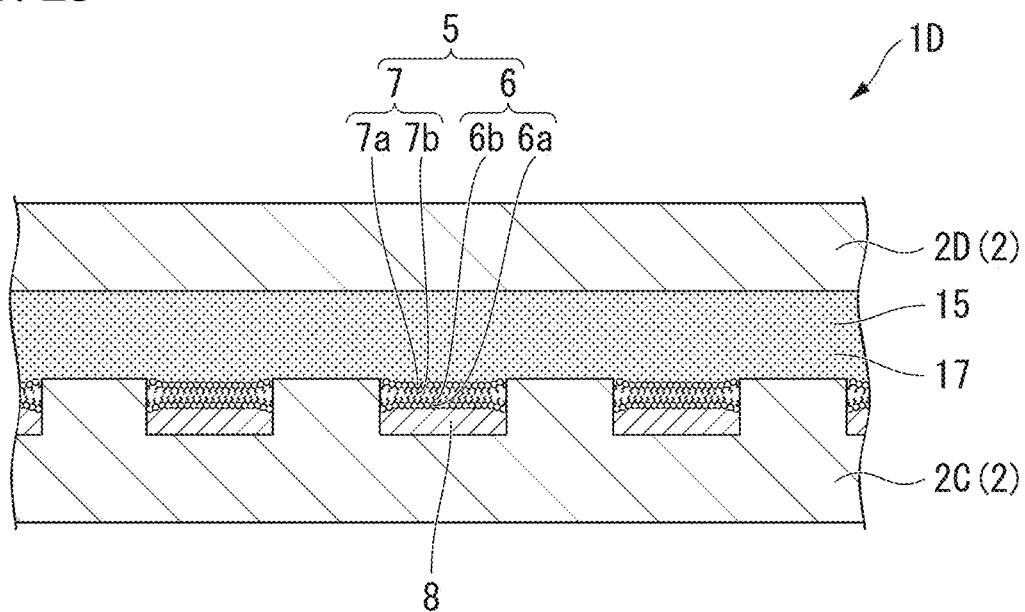
FIG. 23 is a schematic enlarged cross-sectional view showing a membrane vesicle recovery device according to the fifth embodiment of the present invention.

A fifth embodiment of the present invention will be described. FIG. 22 is a cross-sectional view of a membrane vesicle recovery device 1D according to the fifth embodiment of the present invention. The membrane vesicle recovery device according to this embodiment includes a base material (reaction base) 2C having recessed sections 4 and a smooth base material (reaction base) 2D. In addition, the membrane vesicle recovery device according to this embodiment includes a flow path 15 which is provided between the two base materials. The flow path 15 can send a liquid to the recessed sections 4. The recessed sections 4 are filled with a filler 8 through the flow path 15, and an organic solvent containing a lipid solution is sent to the recessed sections 4. Thereafter, an aqueous solvent 17 is then sent to the recessed sections 4. Accordingly, a fused membrane 5 which covers the filler 8 and blocks a recessed section 4 can be coupled to each of the recessed sections 4 as shown in FIG. 23. The type of solvent is not particularly limited as long as this aqueous solvent 17 has a configuration in which a hydrophilic section of the fused membrane 5 faces the aqueous solvent like the buffer solution 16 illustrated in FIGS. 14A and 14B. Examples thereof include a sample such as serum or blood, a reagent, and an aqueous solution such as a buffer. In addition, the aqueous solvent may contain a membrane vesicle.

In the membrane vesicle recovery device according to this embodiment, the recessed sections may be formed of resin, glass, or the like, or may be formed of the same materials as those of the base materials. In addition, the recessed sections may be integrated with the base materials through resin molding processing or the like. The resin can be selected from cycloolefin polymers, silicon, polypropylene, polycarbonate, polystyrene, polyethylene, and polyvinyl acetate, but is not limited thereto. The base material may be formed of a material having rigidity, and may be formed of resin, glass, or the like. In the case of observing micropores through transmission, the base material may be transparent. In addition, a hydrophobic section may be formed through photolithography, and a material such as CYTOP (manufactured by Asahi Glass Co., Ltd.), which is highly hydrophobic, can be selected as the resin.

Next, the membrane vesicle recovery device, the membrane vesicle recovery method, and the membrane vesicle analysis method of this embodiment will be described in more detail based on Examples shown below.

Example 11

(1) Production of Invader Reaction Reagent-Filled Well Plate which is Coated with Lipid Bilayer Membrane A plate made of PDMS and in which micropores (well and recessed sections) with a diameter of 1 μm and a depth of 1 μm were arranged in an array shape by imprinting were prepared. Then, only the well sections were subjected to hydrophilic processing by performing plasma processing using a plasma-generating device. One side of the plate was set to 1 cm and the thickness thereof was set to 5 mm, and $9\times10^6$ wells were arranged in the center. In order to fill the wells with an invader reaction reagent (1 μM allele probe, 0.4 μM invader oligo, 1 μM FAM label arm, 20 μM MOPS pH7.5, 15 mM NaCl, 6.25 mM $MgCl_2$, and 50 U/μL cleavase), 5 μL of a reagent solution was added dropwise to the plate which was then covered with a cover glass. After injecting the reagent solution into the wells under reduced pressure, the cover glass was removed and air-dried.

0.0013 g of oxotitanium phthalocyanine was dissolved in 10 mL of dichloromethane containing 0.1 mol/L trichloroacetic acid to prepare a sample solution for an LB membrane. This sample solution was added dropwise to the water surface to form a monomolecular membrane, and an LB membrane was produced using a commercially available LB membrane production device. The monomolecular membrane was transferred onto the surface of the plate by pulling up the plate in which the wells were filled with the invader reaction reagent and which had been sunk in a water tank in advance. Then, a bilayer membrane was produced after the plate was sunk in the water tank again.

(2) Reaction of Oligonucleotide Sealed in Liposome

An oligonucleotide as a substrate was sealed in a liposome reagent (Thermo Fisher Scientific Inc., Lipofectamine) and was then diluted in stages to obtain a sample solution as a model of an exosome. Thereafter, the sample solution was added dropwise to the top of a well plate filled with an invader reaction reagent of the above-described (1). A cover glass was placed thereon and was lightly pressed. The plate was incubated in an oven at 62° C. for 15 minutes. The fluorescent amount of wells after the reaction was measured (by obtaining an average value of each fluorescent amount of 21 pixels after selecting 5 wells) using a fluorescence microscope (Carl Zeiss, AX10), an objective lens (EC Plan-Neofluar 40×oil NA 1.3), a light source (Lithium Energy Japan, FluoArc 001.26 A Usable with HBO 10), a sensor (Hamamatsu Photonics K.K., EM-CCD C9100), a filter (Olympus Corporation, U-MNIBA2), and analysis software (Hamamatsu Photonics K.K., AQUACOSMOS 2.6: exposure time of 64.3 ms, EM gain of 180, offset of 0, binning×1), and the number of wells exhibiting fluorescence was measured. As a result, it was confirmed that the number of wells exhibiting a constant amount of fluorescence was increased in accordance with the amount of liposome.

Example 2

(1) Production of Membrane Vesicle Recovery Device Having Lipid Bilayer Membrane A glass base material having a thickness of 0.5 mm was spin-coated with CYTOP (manufactured by Asahi Glass Co., Ltd.) and was heat-cured for 3 hours at 180° C., and micropore chips each having one million micropores (well or recessed sections) with a diameter of 5 μm were produced using a photolithography technique. A glass base material with a feeding port was provided on the top of a micropore chip such that the gap between the micropore chips and the glass base became 100 μm. Accordingly, a flow path which is provided between two base materials was produced. The flow path can send a liquid to the micropores. An invader reaction reagent (1 μM allele probe, 0.4 μM invader oligo, 1 μM FAM label arm, 20 μM MOPS pH7.5, 15 mM NaCl, 6.25 mM $MgCl_2$, and 50 U/μL cleavase) was sent to the recessed sections through the sample ports, and the minute recessed sections were filled with the reaction reagent through deaeration. 40 μL of hexadecane in which a mixed lipid of DOPE and DOPG is dissolved to be 4 mg/ml, was sent to the recessed sections. 40 μL of a buffer (20 μM MOPS pH 7.5, 15 mM NaCl, 6.25 mM $MgCl_2$) was sent to the recessed sections.

(2) Reaction of Oligonucleotide Sealed in Liposome

Figure 24:
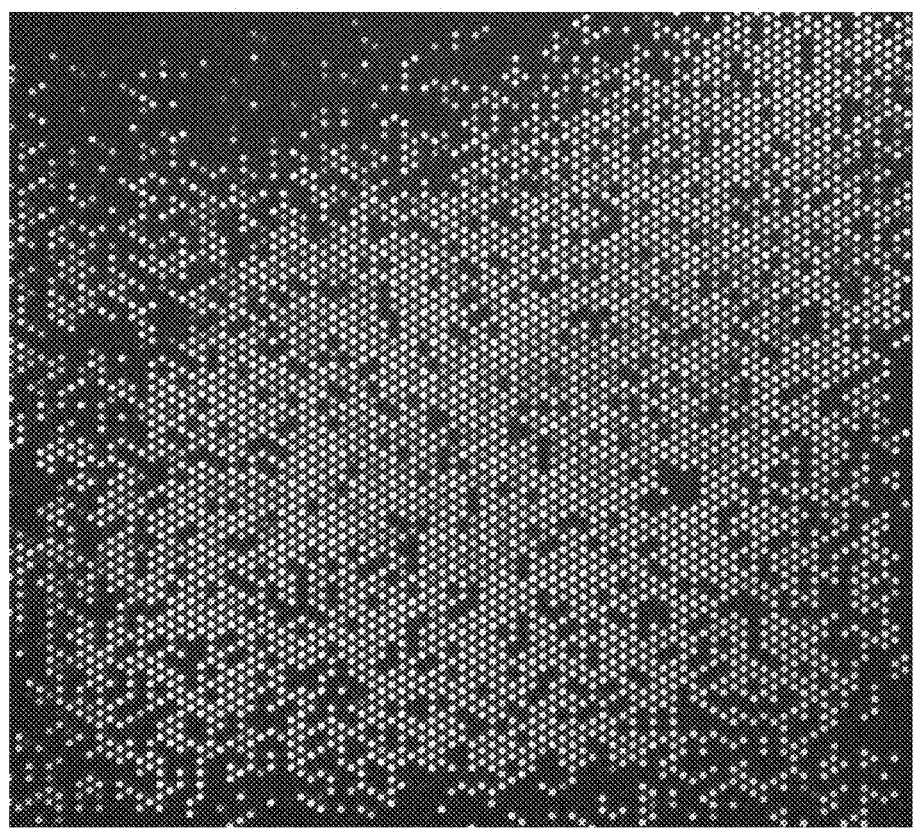
FIG. 24 is a view showing the results in which the fluorescence quantity in wells after reaction in the membrane vesicle recovery device according to the present invention was measured.

An oligonucleotide as a substrate was sealed in a liposome reagent (Thermo Fisher Scientific Inc., Lipofectamine) to obtain a sample solution as a model of an exosome. Thereafter, the sample solution was sent to the top of the wells filled with the above-described invader reaction reagent. The sample solution was made into droplets by further sending oil to the wells. Thereafter, the wells were incubated in an oven at 62° C. for 15 minutes. The fluorescent amount of each well after the reaction was measured using a fluorescence microscope. The measurement results are shown in FIG. 24.

In the above, the embodiments and the examples of the present invention have been described in detail with respect to the drawings. However, specific configurations are not limited to these embodiments, and modifications or the like to the design can be included within a scope not departing from the gist of the present invention.

For example, in the above-described embodiments 3, 4, and 5, the hydrophobic section 7b of the fused membrane 5 may be coupled to the surface 3 of the reaction base 2, as described in the above-described first embodiment.

In addition, the constituents shown in each of the above-described embodiments can be configured by being appropriately combined.

The present invention can be used to separate exosomes, organelles, and other membrane vesicles.

In addition, the present invention can be used in the analysis of constituents of a membrane vesicle.

What is claimed is:

1. A membrane vesicle recovery device, comprising:
a filler;
a first reaction base having a surface on which a plurality of holding sections, each of which is configured to hold the filler, is formed, the filler being in contact with each of the plurality of holding sections;
a second reaction base over the first reaction base, the second reaction base facing the plurality of holding sections;
a flow path between the first and second reaction bases;
a fused membrane for each of the plurality of holding sections, including a lipid bilayer membrane which completely covers an outer periphery of the filler other than a portion where the filler is in contact with the respective holding section,
wherein the filler fills a space surrounded by each of the respective holding sections and the fused membranes; and
the filler contains a reaction reagent for biochemical analysis.

2. The membrane vesicle recovery device according to claim 1, wherein
each of the plurality of holding sections is a recessed section formed in the first reaction base,
in each of the recessed sections, the fused membrane comes into contact with an opening end forming a boundary between the surface and each of the recessed sections and is provided in the first reaction base so as to seal the recessed sections, and
each of the recessed sections is filled with the filler.

3. The membrane vesicle recovery device according to claim 2, wherein
each of the fused membranes is provided in the first reaction base so as to come into contact with a part along the opening end at an inner wall surface of the recessed sections and to individually seal each of the plurality of recessed sections.

4. The membrane vesicle recovery device according to claim 3, wherein
in the first reaction base, at least the surface is hydrophobic, and a hydrophobic section of each fused membrane comes into contact with the surface.

5. The membrane vesicle recovery device according to claim 1, wherein
each of the fused membranes is formed in a planar shape along a surface thereof and seals each of the recessed sections.

6. The membrane vesicle recovery device according to claim 1, wherein
each of the fused membranes contains a membrane charge adjustment substance, for promoting membrane fusion between the fused membrane and a membrane vesicle, which substance is derived from a living body or an artificial vesicle and which is covered by the lipid bilayer membrane.

7. The membrane vesicle recovery device according to claim 6, wherein
the membrane charge adjustment substance contains at least one of a membrane-destroying peptide, a membrane fusogenic polymer, a pH-sensitive polymer, or virus-derived membrane fusion protein.

8. The membrane vesicle recovery device according to claim 1, wherein
the filler further contains a solvent.

9. The membrane vesicle recovery device according to claim 1, wherein
the reaction reagent for biochemical analysis contains a pH indicator.

10. The membrane vesicle recovery device according to claim 1, wherein
the filler is one of liquid, gel or sol.

11. The membrane vesicle recovery device according to claim 1, wherein
the plurality of holding sections is a plurality of hydrophilic sections,
the surface of the first reaction base includes hydrophobic sections surrounding the hydrophilic sections,
the filler is provided in the hydrophilic sections of the first reaction base, and
each of the fused membranes comes into contact with the hydrophobic sections of the first reaction base in a boundary between each of the hydrophilic sections and each of the hydrophobic sections.

12. A membrane vesicle recovery device, according to claim 1, wherein
the filler is configured to be mixed with a content of a membrane vesicle through fusing of the membrane vesicle and the fused membrane.

13. A membrane vesicle recovery device, according to claim 1, wherein
each of the holding sections includes a hydrophobic region and a hydrophilic region.

14. A membrane vesicle recovery device, according to claim 13, wherein
the lipid bilayer membrane includes a hydrophilic section and a hydrophobic section inside the hydrophilic section, and
the hydrophobic section of the lipid bilayer membrane contacts the hydrophobic region of the holding section to cover the holding section by the lipid bilayer membrane.

* * * * *